(12) United States Patent
Adler (10) Patent No.: US 6,897,444 B1
(45) Date of Patent: May 24, 2005

(54) MULTI-PIXEL ELECTRON EMISSION DIE-TO-DIE INSPECTION

(75) Inventor: David L. Adler, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 20 days.

(21) Appl. No.: 10/702,271

(22) Filed: Nov. 6, 2003

Related U.S. Application Data (60) Provisional application No. 60/453,179, filed on Mar. 10, 2003.

(51) Int. Cl.[7] ..................... H01J 37/153; G01N 23/225
(52) U.S. Cl. ...................... 250/310; 250/306; 250/307; 250/311; 250/397; 250/492.2; 250/492.3
(58) Field of Search ................................ 250/310, 306, 250/307, 311, 397, 492.2, 492.3

(56) References Cited

U.S. PATENT DOCUMENTS

| | | | |
|---|---|---|---|
| 4,805,123 A | | 2/1989 | Specht et al. |
| 5,973,323 A | | 10/1999 | Adler et al. |
| 6,087,659 A | * | 7/2000 | Adler et al. ................. 250/310 |
| 6,566,885 B1 | * | 5/2003 | Pinto et al. ................. 324/501 |
| 6,586,733 B1 | * | 7/2003 | Veneklasen et al. ........ 250/306 |

* cited by examiner

Primary Examiner—Nikita Wells
(74) Attorney, Agent, or Firm—Okamoto & Benedicto LLP

(57) ABSTRACT

One embodiment disclosed is a method of detecting defects in objects. A selected surface area of an object is inspected with a multi-pixel electron microscope, and first set of data is generated having signal values representing image content of each pixel thereof. Further selected surface area of the object is inspected with said multi-pixel electron microscope, and second set of data is generated having signal values representing image content of each pixel thereof. Corresponding portions of first and second sets of data are stored in memory. Misalignment between stored portions of the first and second sets of data is detected with resolution of a fraction of a pixel, and the stored portions of first and second sets of data are aligned using subpixel interpolation to correct the detected misalignment therebetween. Finally, corresponding subportions of the aligned portions of first and second sets of data are compared to detect differences therebetween.

25 Claims, 5 Drawing Sheets

MULTI-PIXEL ELECTRON EMISSION DIE-TO-DIE INSPECTION

CROSS-REFERENCE TO RELATED APPLICATIONS

The present application claims the benefit of provisional patent application No. 60/453,179, filed Mar. 10, 2003, entitled "Multi-Pixel Electron Emission Die-to-Die Inspecton", by inventor David L. Adler, the disclosure of which is hereby incorporated by reference.

BACKGROUND OF THE INVENTION

1. Field of the Invention

The present invention relates generally to microscopic inspection methods and apparatus. The present invention relates more particularly to inspection systems for semiconductor manufacturing.

2. Description of the Background Art

A variety of methods have been used to examine microscopic surface structures of semiconductors. These have important applications in the field of semiconductor chip fabrication, where microscopic defects at a surface layer can make the difference between a properly functioning or non-functioning IC. For example, holes or vias in an intermediate insulating layer often provide a physical conduit for an electrical connection between two outer conducting layers. If one of these holes or vias becomes dogged with non-conductive material, this electrical connection between layers will not be established. Automated inspection of the semiconductors is used to ensure a level of quality control in the manufacture of the integrated circuits.

SUMMARY

One embodiment of the invention relates to a method of detecting defects in integrated circuit dies. The method includes directing a first incident beam to be incident on a multi-pixel imaging region from a first die, simultaneously detecting electrons emitted from a plurality of pixels within the multi-pixel imaging region, and generating a first image data set comprising signal values representing image content of the plurality of pixels within the multi-pixel imaging region. The method also includes directing a second incident beam to be incident on a corresponding multi-pixel imaging region from a second die, simultaneously detecting electrons emitted from a plurality of pixels within the corresponding multi-pixel imaging region, and generating a second image data set comprising signal values representing image content of the plurality of pixels within the corresponding multi-pixel imaging region. The first and second image data sets are stored in memory. Misalignment between the first and second image data sets is determined with a resolution of a fraction of one pixel. The image data sets are aligned by adjusting one of the image data sets to correct the misalignment, and the aligned first and second image data sets are compared to detect differences therebetween.

Another embodiment of the invention relates to a method of detecting defects in objects. A selected surface area of an object is inspected with a multi-pixel electron microscope, and a first set of data is generated having signal values representing image content of each pixel thereof. A further selected surface area of the object is inspected with said multi-pixel electron microscope, and a second set of data is generated having signal values representing image content of each pixel thereof. Corresponding portions of the first and second sets of data are stored in memory. Misalignment between the stored portions of the first and second sets of data is detected with resolution of a fraction of a pixel, and the stored portions of the first and second sets of data are aligned using subpixel interpolation to correct the detected misalignment therebetween. Finally, corresponding subportions of the aligned portions of the first and second sets of data are compared to detect differences therebetween.

Another embodiment of the invention relates to an apparatus for detecting defects in integrated circuit dies. The apparatus includes an incident beam system, a multi-pixel electron detector, a memory operatively coupled to the detector, and a processor operatively coupled to the memory. The incident beam system impinges an incident beam onto a multi-pixel imaging region of a first die and a corresponding multi-pixel imaging region of a second die. The multi-pixel electron detector simultaneously detects electrons emitted from a plurality of pixels within the multi-pixel imaging regions and generates first and second image data sets therefrom, wherein the first image data set is from the first die and the second image data set is from the second die. The memory stores the first and second image data sets. The processor determines a misalignment between the first and second image data sets with a resolution of a fraction of one pixel. The processor also aligns the image data sets by adjusting one of the image data sets to correct the misalignment. Finally, the processor compares the aligned first and second image data sets to detect differences therebetween.

Another embodiment of the invention relates to apparatus of detecting defects in objects. The apparatus includes a multi-pixel electron microscope, a memory system, a misalignment detection means operatively coupled to the memory system, an aligning means operatively the misalignment detection means and to the memory system, and a comparison means operatively coupled to the memory system. The multi-pixel electron microscope inspects a selected surface area of an object and generates a first set of data having signal values representing image content of each pixel thereof. The multi-pixel electron microscope also inspects a further selected surface area of the object and generates a second set of data having signal values representing image content of each pixel thereof. The memory system stores corresponding portions of the first and second sets of data. The misalignment detection means detects a misalignment between the stored portions of the first and second sets of data with a resolution to a fraction of a pixel. The aligning means aligns the stored portions of the first and second sets of data using subpixel interpolation to correct the detected misalignment therebetween. Finally, comparison means compares corresponding subportions of the aligned portions of the first and second sets of data to detect differences therebetween, and upon detecting a difference, indicates presence of a defect at a particular pixel location on the inspected object.

DETAILED DESCRIPTION

U.S. Pat. No. 4,805,123, inventors Sprecht et al., issued Feb. 14, 1989 ("the Sprecht patent"), describes an optically-based method and apparatus for automatic photomask and reticle inspection. In the Sprecht patent, portions of an optically inspected photomask or the like are compared with other portions of the same mask or to data corresponding to similar portions stored in a preexisting database.

However, the optically-based method and apparatus of the Sprecht patent has various disadvantages. Light beams have an inherent resolution limit of about 100 nm–200 nm. This limits the size of defects that can be detected to relatively large defects. X-rays (photons with shorter wavelengths) has improved resolution over light, but x-rays are difficult to produce and manipulate.

Furthermore, optical beams disadvantageously tend to produce false positives in semiconductor defect inspection. Optical beams are sensitive to problems of color noise and grain structures, and these problems tend to produce false positives. Oxide trenches and polysilicon lines are especially prone to false positives with optical beams due to grain structure.

The present invention overcomes the above-described disadvantages and so arrives at an improved and advantageous method and apparatus for microscopic inspection. The limited resolution and false positives of the optical inspection technique in the Sprecht patent are overcome by utilizing an electron emission inspection technique. Moreover, instead of conventional scanning electron microscopy (SEM), where a narrow beam of primary electrons is raster-scanned across the surface of the wafer, the present invention employs a multi-pixel incident beam to advantageously obtain information from multiple pixels in parallel. Obtaining information from multiple pixels in parallel results in improved throughput for the inspection system.

Figure 1A:
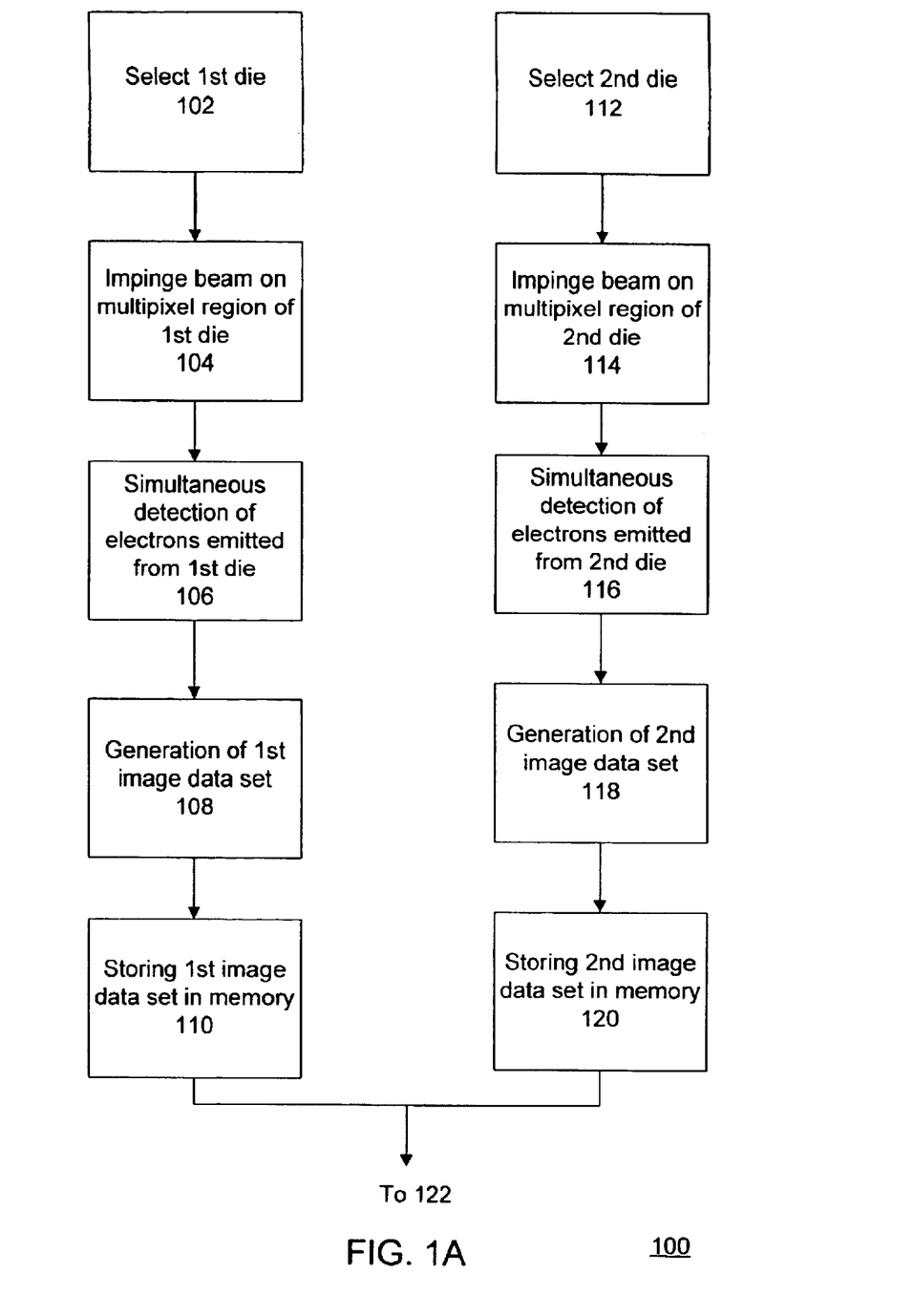
FIGS. 1A and 1B depict a method for detecting defects in integrated circuit dies in accordance with an embodiment of the invention.
Figure 1B:
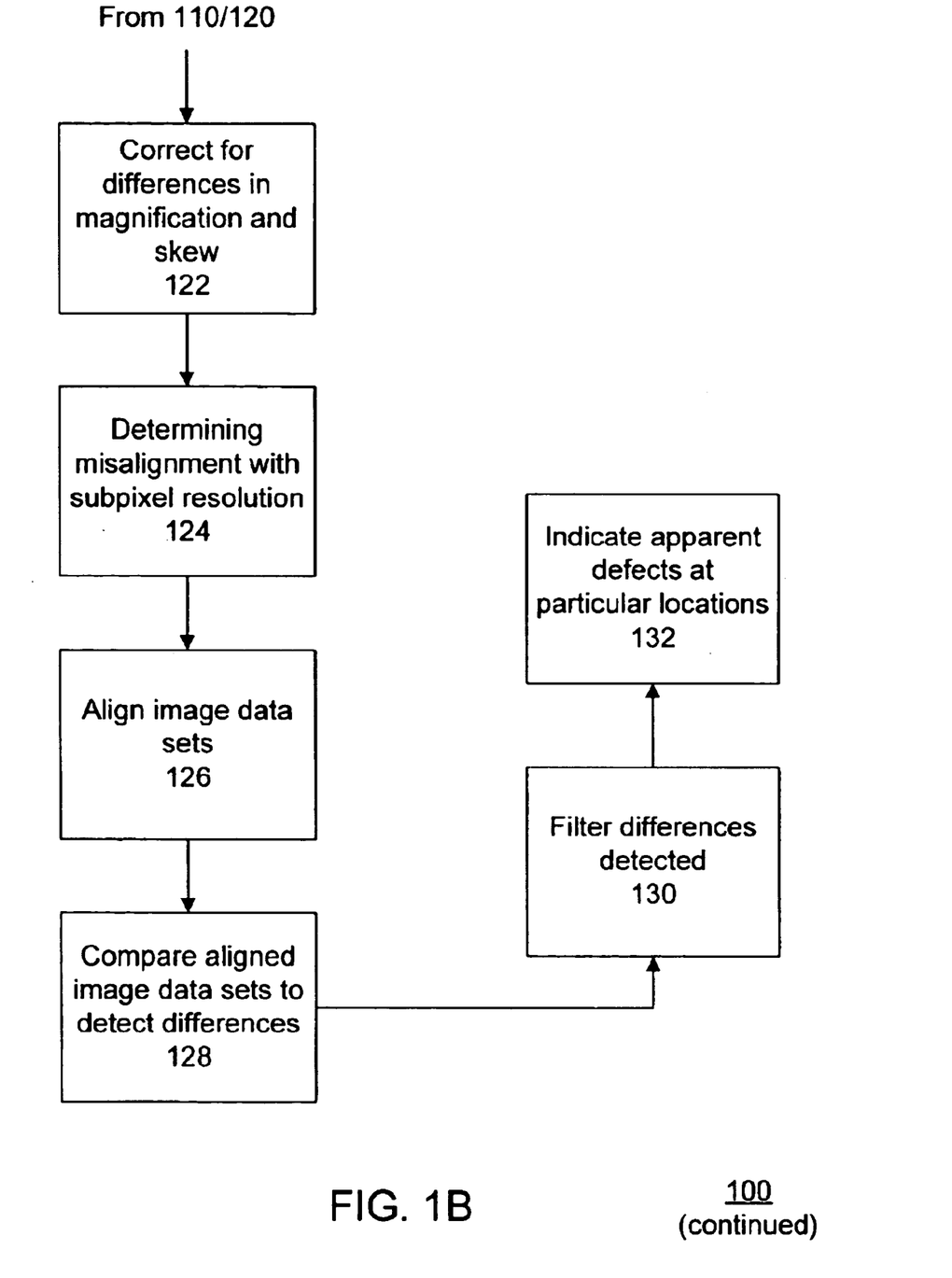

FIGS. 1A and 1B depict a method 100 for detecting defects in integrated circuit dies in accordance with an embodiment of the invention. FIG. 1A depicts ten steps (102, 104, 106, 108, 110, 112, 114, 116, 118, and 120) of the method 100. The first set of five steps (102, 104, 106, 108, and 110) relate to obtaining image data from a first selected integrated circuit die, and the second set of five steps (112, 114, 116, 118, and 120) relate to obtaining image data from a second selected integrated circuit die. FIG. 1B depicts six subsequent steps (122, 124, 126, 128, 130 and 132) of the method 100 where the image data are aligned and compared to detect defects.

In the first step 102, a first die is selected. In one embodiment, the first die may be a reference die that is used as a standard for comparison to other dies to determine defects in the other dies. Alternatively, the first die may be to selected via a random inspection mode from among dies on a semiconductor wafer.

In the second step 104, an incident beam spot is impinged upon a region of the first die. The incident spot is adjusted to be of sufficient size and uniformity to advantageously support multi-pixel detection from the region. For example, in one embodiment, the incident beam spot may have a usable diameter in the range of 0.1 to 100 millimeters and may comprise electrons at an energy level that results in a stable balance between incident and emitted electrons. Such electrons generate secondary electrons from the illuminated region. This higher energy level is referred to as energy level $E_2$ in U.S. Pat. No. 5,973,323, inventors Adler et al., issued Oct. 26, 1999 to KLA-Tencor Corporation. U.S. Pat. No. 5,973,323 is hereby incorporated by reference in its entirety.

In an alternate embodiment, the incident beam spot may comprise low-energy electrons under about one hundred electron volts in energy. Such low-energy electrons generate reflected electrons from the illuminated region. One disadvantage with using low-energy electrons is that a negative charge build-up can occur on the surface of the specimen. This is because at such low energies, more primary electrons are incident than scattered electrons are emitted. In yet another possible embodiment, the incident beam spot may comprise photons at a sufficiently high energy level to generate photo electrons from the illuminated region.

In the third step 106, scattered electrons (secondary or reflected or photo) emitted from multiple pixels of the illuminated region of the first die are "simultaneously" detected. In other words, the electrons emitted from the pixels are detected in parallel. Such parallel detection may be accomplished, for example, using a time delay integrating (TDI) electron detector, or alternatively, using a camera. In the fourth step 108, a first image data set is generated from the detected electrons. The image data set indicates the intensity of emitted electrons detected from each pixel of the multi-pixel illuminated region. The first image data set is stored in the fifth step 110. The storage may be implemented in a form of computer-readable memory, for example, as part of an inspection system.

The sixth 112, through tenth 120 steps are similar to the first 102 through fifth 110 steps. However, the sixth 112 through tenth 120 steps relate to a second integrated circuit die. The second die has the same integrated circuit as the first die. Note that the sixth 112 through tenth 120 steps may be performed after the first 102 through fifth 110 steps. Alternatively, the sixth 112 through tenth 120 steps may be performed in parallel with the first 102 through fifth 110 steps.

In the sixth step 112, the second die is selected for comparison against the first die. In one embodiment, the second die may be selected, for example, at random from among dies on the wafer. Alternatively, the second die may be selected sequentially so as to eventually inspect all the dies on the wafer.

In the seventh step 114, an incident beam spot is impinged upon the region of the second die that corresponds to the impinged region of the first die. The corresponding region is impinged because the image data from the first and second dies are to be compared in order to detect defects therein.

In the eighth step 116, scattered electrons (secondary or reflected or photo) emitted from multiple pixels of the illuminated region of the second die are "simultaneously" detected. The second image data set is generated from the detected electrons in the ninth step 118. The second image data set indicates the intensity of emitted electrons detected from each pixel of the multi-pixel illuminated region of the second die. In the tenth step 120, the second image data set is stored in a form of computer-readable memory.

Once both the first image data set and the second image data set are stored, the method 100 moves on to the eleventh 122 through sixteenth 132 steps shown in FIG. 1B.

In the eleventh step 122, correction is made for differences in magnification and skew between the first and second images. In one embodiment of the invention, the correction may be accomplished utilizing bilinear interpolation. An example of bilinear interpolation is explained in the Sprecht patent in relation to FIG. 4 therein.

In the twelfth step 124, misalignment between the first image and the second image is determined. The misalignment determination is made with sub-pixel resolution and may include both a misalignment vector and skew (rotation). In one embodiment, for example, the misalignment determination may be implemented in accordance with the process described below in relation to FIG. 4.

In the thirteenth step 126, the two image data sets are aligned using the misalignment determined in the twelfth step 124. If the misalignment determined comprised a misalignment vector of the second image with respect to the first image, then the second image data set may be shifted by the misalignment vector in a way such that the second image data set becomes aligned with the first image data set.

In the fourteenth step 128, the two aligned image data sets are compared against each other to detect differences therebetween. Some of the differences may be insubstantial and so not correspond to an actual defect. Other differences will be substantial and correspond to actual defects. Hence, filtering of the differences detected may be applied in the fifteenth step 130. For example, the filtering may include a threshold function or a more complex function.

Finally, those differences that pass the filtering of the fifteenth step 130 are deemed to apparently relate to defects. The apparent defects and their particular locations are indicated in the sixteenth step 132. For example, if the first die is deemed to be a reference die, then the apparent defects and their location in the second die may be indicated.

Figure 2:
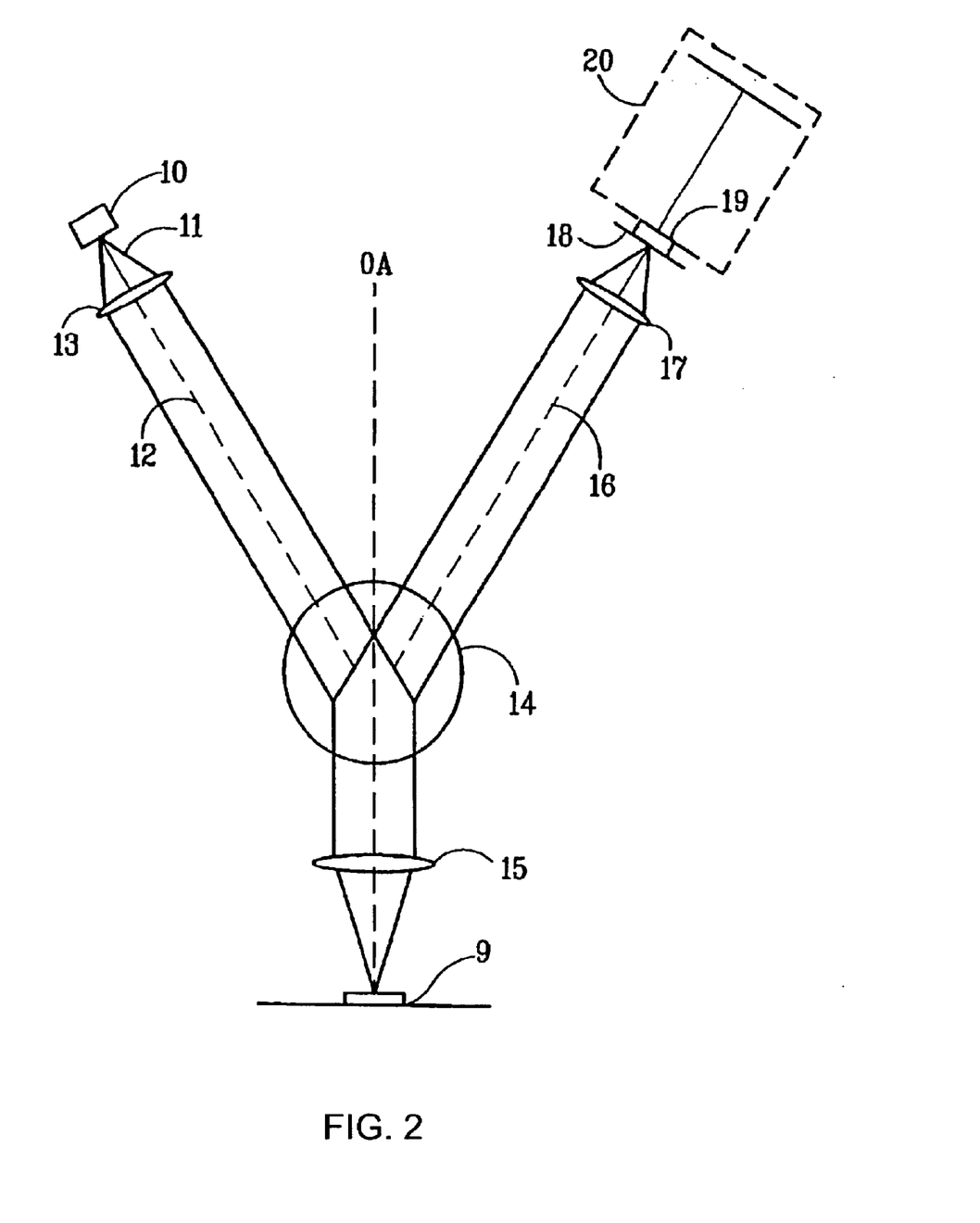
FIG. 2 depicts an apparatus for generating a multi-pixel electron beam in accordance with an embodiment of the invention.

FIG. 2 depicts an apparatus for generating a multi-pixel electron beam in accordance with an embodiment of the invention. The apparatus shown in FIG. 2 comprises a secondary electron emission microscope (SEEM). In summary, the apparatus forms a relatively large electron beam spot (rather than a small one) at the surface of the wafer, and secondary electrons emitted from this spot are imaged onto a two-dimensional detector. Typically, the specimen may comprise a semiconductor wafer having integrated circuit related structures formed on its surface.

More specifically, an electron gun source 10 emits a beam 11 of primary electrons $e_1$ along path 12. The electron beam 11 is collimated by electron lens 13 and continues along path 12. Magnetic beam separator 14 then bends the collimated electron beam 11 to be incident along electron optical axis OA normal to the surface to be inspected. Objective electron lens 15 focuses the primary electrons, $e_1$, into a beam having a spot size typically in the range 1–10 mm and an incident energy on the order of 1 keV on specimen 9.

Primary electrons $e_1$ incident on the specimen 9 produce secondary electrons $e_2$ which travel back along the axis OA perpendicular to the inspection surface to objective electron lens 15, where they are re-collimated. Magnetic beam separator 14 bends the electrons to travel along image path 16. The electron beam along image path 16 is focused by projection electron lens 17 to image plane 18, where there is an electron detector 19, which is a camera or preferably a time delay integrating (TDI) electron detector. The operation of an analogous TDI optical detector is disclosed in U.S. Pat. No. 4,877,326, entitled "Method and Apparatus for Optical Inspection of Substrates," inventors Chadwick et al., and assigned at issuance to KLA Instruments Corporation. The disclosure of U.S. Pat. No. 4,877,326 is incorporated herein by reference. The image information may be processed directly from a 'back thin' TDI electron detector 19, or the electron beam may be converted into a light beam and detected with an optional optical system 20 and a TDI optical detector. The operation of the system of FIG. 2 is further described in U.S. Pat. No. 5,973,323.

In alternative to the SEEM apparatus of FIG. 2, other apparatus may be utilized for generating a multi-pixel electron beam. For example, a low energy electron microscope (LEEM) apparatus may instead be used. Such a LEEM apparatus employs low energy incident electrons and detects reflected electrons from the surface of the wafer. As another example, a photo-electron emission microscope (PEM or PEEM) apparatus may instead be used. Such a PEEM apparatus employs incident photons and detects photo-electrons emitted from the illuminated surface of the wafer. One advantage of using the SEEM apparatus (over using a LEEM apparatus or a PEEM apparatus) is that surface charging may be reduced.

Figure 3:
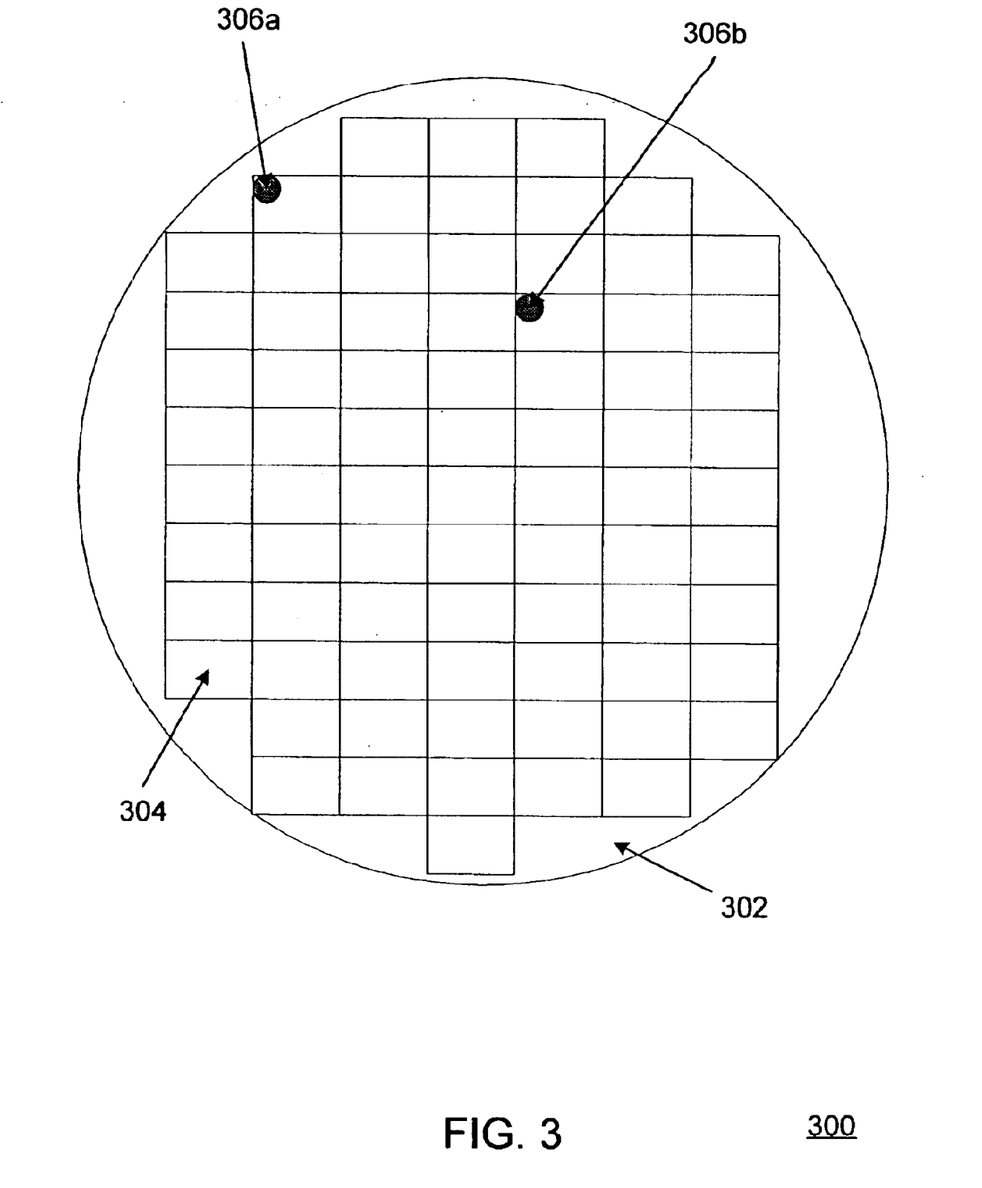
FIG. 3 depicts corresponding regions of integrated circuit dies on a semiconductor wafer in accordance with an embodiment of the invention.

FIG. 3 depicts corresponding regions of first and second integrated circuit dies on a semiconductor wafer in accordance with an embodiment of the invention. FIG. 3 illustrates a semiconductor wafer 302 on the surface of which numerous integrated circuit dies 304 are fabricated. Two dies are of particular interest in this instance. The first die includes a region 306a that is illuminated by an incident beam. The second die includes a corresponding region 306b that is also illuminated by an incident beam. Image data from the two corresponding regions (306a and 306b) are then aligned, compared, and analyzed to detect defects in accordance with an embodiment of the present invention.

In one particular embodiment, the region 306b of the second die may be illuminated after the region of the first die is illuminated. This may be the case, for example, when the first die corresponds to a reference die. Alternatively, with equipment capable of producing two incident beams, both dies may be illuminated in parallel. In another variation, the first die and the second die may be on different wafers (though the wafers would still have the same integrated circuit dies formed thereon).

Figure 4:
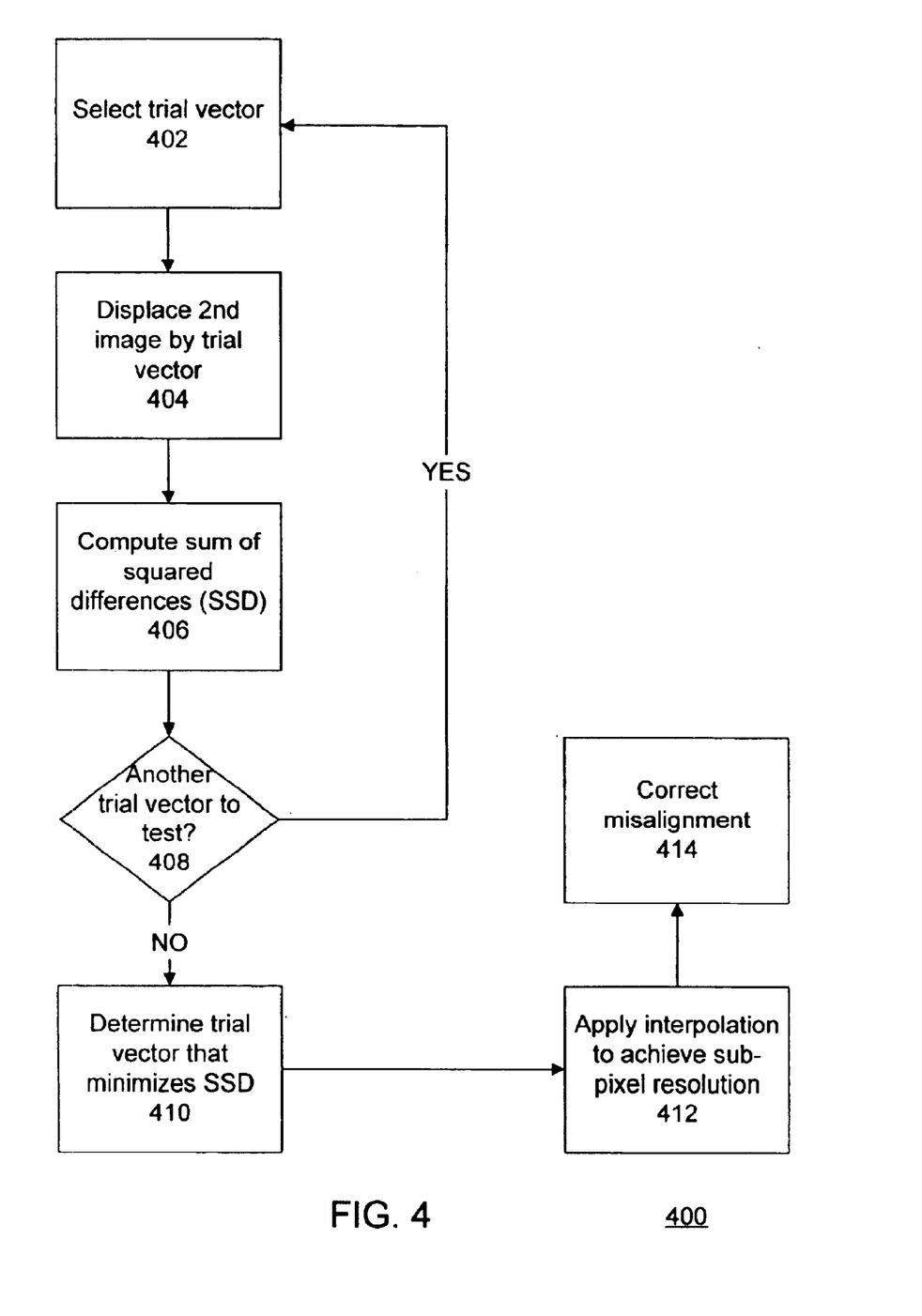
FIG. 4 depicts a method for correcting misalignment with sub-pixel resolution in accordance with an embodiment of the invention.

FIG. 4 depicts a method for correcting misalignment with sub-pixel resolution in accordance with an embodiment of the invention. The method 400 as depicted includes seven steps (402, 404, 406, 408, 410, 412, and 414).

In the first step 402, a trial vector is selected from a set of trial vectors. The set of trial vectors is made broad enough to cover the anticipated range of displacements needed to align the second image data set to the first image data set. In accordance with one embodiment, the set may include trial vectors at a same density as the pixel density. In that case, interpolation may subsequently be utilized to achieve higher precision (to sub-pixel resolution) in the alignment correction. Such an interpolation is described below in relation to the sixth step 412.

In the second step 404, the second image data set is displaced by the selected trial vector and rotated by the selected trial skew (rotation). The resolution or fineness of the alignment correction will depend on the density of trial vectors and skews within the set. In accordance with an embodiment of the invention, sub-pixel resolution is utilized to advantageously accomplish a fine level in the alignment correction. For example, in a specific embodiment, alignment correction with sub-pixel resolution may be accomplished using sub-pixel bilinear interpolation.

In the third step 406, a sum of squared differences (SSD) or other similar measure is computed. The SSD is an indication of the alignment between the two image data sets after the second image data set is displaced and rotated by a particular trial vector and skew. Generally speaking, the lower the SSD value, the better the match between the two data sets.

In the fourth step 408, a determination is made as to whether there is another trial vector in the set of trial vectors to test. If there is, then the process 400 goes back to the first step 402. Otherwise, the process 400 moves on to the fifth step 410.

In the fifth step 410, a determination is made as to which trial vector corresponded to a minimum SSD value. That vector is deemed to be the closest of the trial vectors for correcting the misalignment. However, in order to achieve higher resolution in the misalignment correction, the sixth step 412 may be utilized. The sixth step 412 uses interpolation to increase the resolution. In one embodiment, the interpolation algorithm may be based on the assumption that the SSD surface is locally parabolic in the region of the minimum SSD value. An example of an interpolation algorithm that may be used for this purpose is discussed in the Sprecht patent.

Finally, in the seventh step 414, the misalignment correction is applied to the second image data set. This aligns the second image data set to the first image data set prior to the detection of differences between the two.

The above-described diagrams are not necessarily to scale and are intended be illustrative and not limiting to a particular implementation. The above-described invention may be used in an automatic inspection or review system and applied to the inspection or review of wafers, X-ray masks and similar substrates in a production environment. While it is expected that the predominant use of the invention will be for the inspection or review of wafers, optical masks, X-ray masks, electron-beam-proximity masks and stencil masks, the techniques disclosed here may be applicable to the high speed electron beam imaging of other samples.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method of detecting defects in integrated circuit dies, the method comprising:
    directing a first incident beam to be incident on a multi-pixel imaging region from a first die;
    simultaneously detecting electrons emitted from a plurality of pixels within the multi-pixel imaging region;
    generating a first image data set comprising signal values representing image content of the plurality of pixels within the multi-pixel imaging region;
    directing a second incident beam to be incident on a corresponding multi-pixel imaging region from a second die;
    simultaneously detecting electrons emitted from a plurality of pixels within the corresponding multi-pixel imaging region;
    generating a second image data set comprising signal values representing image content of the plurality of pixels within the corresponding multi-pixel imaging region;
    storing the first and second image data sets in memory;
    determining a misalignment between the first and second image data sets with a resolution of a fraction of one pixel;
    aligning the image data sets by adjusting one of the image data sets to correct the misalignment; and
    comparing the aligned first and second image data sets to detect differences therebetween.

2. The method of claim 1, further comprising:
    indicating a presence of an apparent defect at a particular location where a difference is detected.

3. The method of claim 2, wherein the apparent defect is indicated only if the detected difference is greater than a threshold difference.

4. The method of claim 1, wherein the first and second incident beams are generated by a same column at different times.

5. The method of claim 1, wherein the first and second incident beams are generated by two different columns.

6. The method of claim 1, wherein determining the misalignment comprises finding an adjustment that a sum of squared differences between the two image data sets is minimized.

7. The method of claim 1, wherein the misalignment comprises a misalignment vector that has subpixel resolution, and wherein the adjustment comprises translation by the misalignment vector.

8. The method of claim 1, wherein the misalignment comprises a skew, and wherein the adjustment comprises rotation to correct the skew.

9. The method of claim 1, wherein the incident beams comprise low energy electron beams, and wherein the emitted electrons comprise reflected electrons.

10. The method of claim 1, wherein the emitted electrons comprise secondary electrons.

11. A method of detecting defects in objects, the method comprising:
    inspecting a selected surface area of an object with a multi-pixel electron microscope and generating a first set of data having signal values representing image content of each pixel thereof;
    inspecting a further selected surface area of the object with said multi-pixel electron microscope and generating a second set of data having signal values representing image content of each pixel thereof;
    storing corresponding portions of the first and second sets of data in memory;
    detecting a misalignment between the stored portions of the first and second sets of data with a resolution to a fraction of a pixel;
    aligning the stored portions of the first and second sets of data using subpixel interpolation to correct the detected misalignment therebetween; and
    comparing corresponding subportions of the aligned portions of the first and second sets of data to detect differences therebetween, and upon detecting a difference.

12. The method of claim 11, further comprising indicating presence of a defect at a particular pixel location on the inspected object.

13. The method of claim 11, wherein the multi-pixel electron microscope comprises a multi-pixel low energy emission microscope (LEEM), and wherein image content is generated from reflected electrons.

14. The method of claim 11, wherein the multi-pixel electron microscope comprises a photo-electron emission microscope (PEEM), and wherein image content is generated from photo-electrons.

15. The method of claim 11, wherein the multi-pixel electron microscope comprises a secondary electron emission microscope (SEEM), and wherein image content is generated from photo-electrons.

16. An apparatus for detecting defects in integrated circuit dies, the apparatus comprising:

an incident beam system to impinge an incident beam onto a multi-pixel imaging region of a first die and a corresponding multi-pixel imaging region of a second die;

a multi-pixel electron detector for simultaneously detecting electrons emitted from a plurality of pixels within the multi-pixel imaging regions and for generating first and second image data sets therefrom, wherein the first image data set is from the first die and the second image data set is from the second die;

a memory operatively coupled to the detector for storing the first and second image data sets;

a processor operatively coupled to the memory for determining a misalignment between the first and second image data sets with a resolution of a fraction of one pixel, aligning the image data sets by adjusting one of the image data sets to correct the misalignment, and comparing the aligned first and second image data sets to detect differences therebetween.

17. The apparatus of claim 16, wherein the processor further indicates an apparent defect at a particular location where a difference is detected.

18. The apparatus of claim 17, wherein the apparent defect is indicated only if the detected difference is greater than a threshold difference.

19. The apparatus of claim 16, wherein the processor determines the misalignment by finding an adjustment such that a sum of squared differences between the two image data sets is minimized.

20. The apparatus of claim 16, wherein the misalignment comprises a misalignment vector that has subpixel resolution, and wherein the adjustment comprises translation by the misalignment vector.

21. The apparatus of claim 16, wherein the misalignment comprises a skew, and wherein the adjustment comprises rotation to correct the skew.

22. The apparatus of claim 16, wherein the incident beam comprises a low energy electron beam, and wherein the emitted electrons comprise reflected electrons.

23. The apparatus of claim 16, wherein the incident beam comprises a primary electron beam, and wherein the emitted electrons comprise secondary electrons.

24. The apparatus of claim 16, wherein the incident beam comprises a photon beam, and wherein the emitted electrons comprise photo-electrons.

25. An apparatus of detecting defects in objects, the apparatus comprising:

a multi-pixel electron microscope for inspecting a selected surface area of an object and generating a first set of data having signal values representing image content of each pixel thereof, and for inspecting a further selected surface area of the object and generating a second set of data having signal values representing image content of each pixel thereof;

a memory system operatively coupled to the multi-pixel electron microscope for storing corresponding portions of the first and second sets of data;

misalignment detection means operatively coupled to the memory system for detecting with a resolution to a fraction of a pixel a misalignment between the stored portions of the first and second sets of data;

aligning means operatively coupled to the misalignment detection means and to the memory system for aligning the stored portions of the first and second sets of data using subpixel interpolation to correct the detected misalignment therebetween; and comparison means operatively coupled to the memory system for comparing corresponding subportions of the aligned portions of the first and second sets of data to detect differences therebetween, and upon detecting a difference, indicating presence of a defect at a particular pixel location on the inspected object.

* * * * *